United States Patent [19]

Maeda et al.

[11] Patent Number: 5,276,610
[45] Date of Patent: Jan. 4, 1994

[54] DISPLAY DEVICE FOR INDICATING THE INTERNAL PRESSURE OF THE TUBE OF AN INFUSION PUMP

[75] Inventors: Akihiro Maeda, Kyoto; Masafumi Kawahara, Nara, both of Japan; Edmund D. D'Silva, Highland Park, Ill.; Larry Kramer, Chicago, Ill.; Kenneth M. Lynn, McHenry, Ill.

[73] Assignees: Sharp Kabushiki Kaisha, Osaka, Japan; Baxter International, Inc., Ill.

[21] Appl. No.: 513,883

[22] Filed: Apr. 24, 1990

[30] Foreign Application Priority Data

Apr. 28, 1989 [JP] Japan .................. 1-50547[U]

[51] Int. Cl.⁵ .......................................... G06F 15/42
[52] U.S. Cl. ........................................... 364/413.02
[58] Field of Search ............. 364/413.02; 340/720-; 128/748

[56] References Cited

U.S. PATENT DOCUMENTS

| | | |
|---|---|---|
| 3,690,318 | 9/1972 | Gorsuch . |
| 4,140,110 | 2/1979 | Jansen et al. . |
| 4,192,319 | 3/1980 | Hargens et al. . |
| 4,209,023 | 6/1980 | Layton . |
| 4,277,227 | 7/1981 | Jenkins . |
| 4,392,847 | 7/1983 | Whitney et al. . |
| 4,395,259 | 7/1983 | Prestele et al. . |
| 4,455,558 | 6/1984 | Williams ............... 340/722 |
| 4,457,751 | 7/1984 | Rodler .................. 604/67 |
| 4,468,219 | 8/1984 | George et al. . |
| 4,534,756 | 8/1985 | Nelson . |
| 4,559,038 | 12/1985 | Berg et al. . |
| 4,648,869 | 3/1987 | Bobo, Jr. . |
| 4,657,529 | 4/1987 | Prince et al. . |
| 4,689,615 | 8/1987 | Del Rosso ............... 340/722 |
| 4,710,163 | 12/1987 | Butterfield . |
| 4,711,248 | 12/1987 | Stuer et al. ............. 128/748 |
| 4,846,792 | 7/1989 | Bobo, Jr. et al. . |

FOREIGN PATENT DOCUMENTS

| | | |
|---|---|---|
| 1170528 | 7/1984 | Canada . |
| 0266632 | 10/1987 | European Pat. Off. ....... G06F 9/30 |
| 59-155261 | 9/1984 | Japan . |

OTHER PUBLICATIONS

"Interstitial Fluid Pressure in Muscle and Compartment Syndromes in Man," Hargens et al, Microvascular Research 14, (1977) (pp. 1-10).

Primary Examiner—Gail O. Hayes

[57] ABSTRACT

A display device for indicating the internal pressure of a tube of an infusion device having an infusion drive for supplying an infusion fluid from a solution container to the human body through the tube and a sensor for detecting the internal pressure of the tube. The display device includes a message indicator for displaying the internal pressure of the tube as detected by the sensor. The message indicator has a plurality of alphanumeric display elements each consisting of a plurality of segments. The display elements are used to display a value, in alphanumeric terms, of the internal pressure of the tube. Further, some of the segments of the display elements are used to display the quantitative change of the pressure as a bar graph.

9 Claims, 3 Drawing Sheets

DISPLAY DEVICE FOR INDICATING THE INTERNAL PRESSURE OF THE TUBE OF AN INFUSION PUMP

BACKGROUND OF THE INVENTION

1. Field of the Invention

The present invention relates to a display device for indicating the internal pressure of the tube of an infusion device, and more particularly, to a display device for informing the user such as a nurse or hospital staff of the pressure detected by an occlusion detector mounted on the downstream of the tube of the infusion device for supplying an infusion fluid from a solution container to the human body through the tube.

2. Description of the Related Art

Conventionally, in a medical infusion device, an infusion drive disposed on the tube thereof operates to infuse a fluid from a solution container to the human body through the tube. There are cases where a partial or total occlusion occurs in the tube between the infusion device and the patient. In order to detect such an occlusion, an occlusion detector comprising a sensor for detecting the tube internal pressure is mounted in the downstream side of an infusion drive means. The occlusion detector is connected to a microcomputer for controlling the operation of the infusion drive means. If the internal pressure of the tube exceeds a predetermined pressure, the operation of the infusion drive means is suspended and an alarm sounds based on the decision that the tube has been occluded.

As apparent from the above, conventionally, it is not until an alarm is given as a result of the stop of the infusion supply operation due to the occurrence of a tube occlusion that the user such as a nurse or hospital staff is informed of the tube occlusion. Such being the case, it is necessary for the user to carry out a troublesome work in order to resume the infusion supply operation. In addition, known medical infusion device has a disadvantage that the infusion supply operation is suspended although a patient requires a continuous supply of infusion. Further, it is necessary to check the cause of the tube occlusion and whether or not the tube occlusion has been already released. Thus, it takes time and labor to resume the infusion supply operation.

SUMMARY OF THE INVENTION

The present invention has been made with a view to substantially solving the above-described disadvantage. Its essential object is to provide a display device for continuously indicating the quantitative change of the tube internal pressure detected by a tube occlusion detector, as information easily observable, so that the cause of the tube occlusion can be removed before the infusion supply operation is stopped.

In accomplishing these and other objects, the present device provides a display device for indicating the internal pressure of the tube of an infusion device including an infusion tube, an infusion drive means for pressure delivery of an infusion fluid to the human body or the like through said tube and a sensor attached to said tube and adapted to detect the internal pressure of said tube, characterized in that said display device comprises a message indicator adapted to indicate the tube internal pressure detected by said sensor and provided with display elements for displaying the content of the sensor-detected pressure in alphanumeric terms and, by utilizing some segments of said display element, indicate the quantitative change in sensor-detected pressure as a bar graph.

More specifically, the sensor outputs data indicative of a detected pressure to a microcomputer which, in turn, compares the data inputted thereto with a data indicative of a predetermined tube occlusion detecting reference pressure so as to decide whether or not the internal pressure of the tube is greater than the predetermined tube occlusion detecting reference pressure. Based on the decision, the display elements of the message indicator connected to said microcomputer are energized. If the internal pressure of the tube has reached the predetermined tube occlusion detecting reference pressure, the operation of the infusion drive means is stopped by the microcomputer.

As the display elements of the message indicator, alphanumeric or 7-segment numeric display elements are used and utilizing some segments of such display elements, for example, the horizontal bar segments at the bottom line, it is so arranged that as the internal pressure of the tube increases, the number of horizontal bar segments energized increases to extend the bar length.

Since the quantitative change of the internal pressure of the tube is displayed by means of a bar graph as described above, the user can easily find the change of the internal pressure of the tube. Accordingly, when the tube has been occluded by a patient's turning in bed or the like, the nurse can remove the cause before an ultimate tube occlusion results in an arrest of pressure delivery.

BRIEF DESCRIPTION OF THE INVENTION

These and other objects and features of the present invention will become apparent from the following description taken in conjunction with preferred embodiments thereof with reference to the accompanying drawings, throughout which like parts are designated by like reference numerals, and in which.

DETAILED DESCRIPTION OF THE INVENTION

Figures 1, 2:
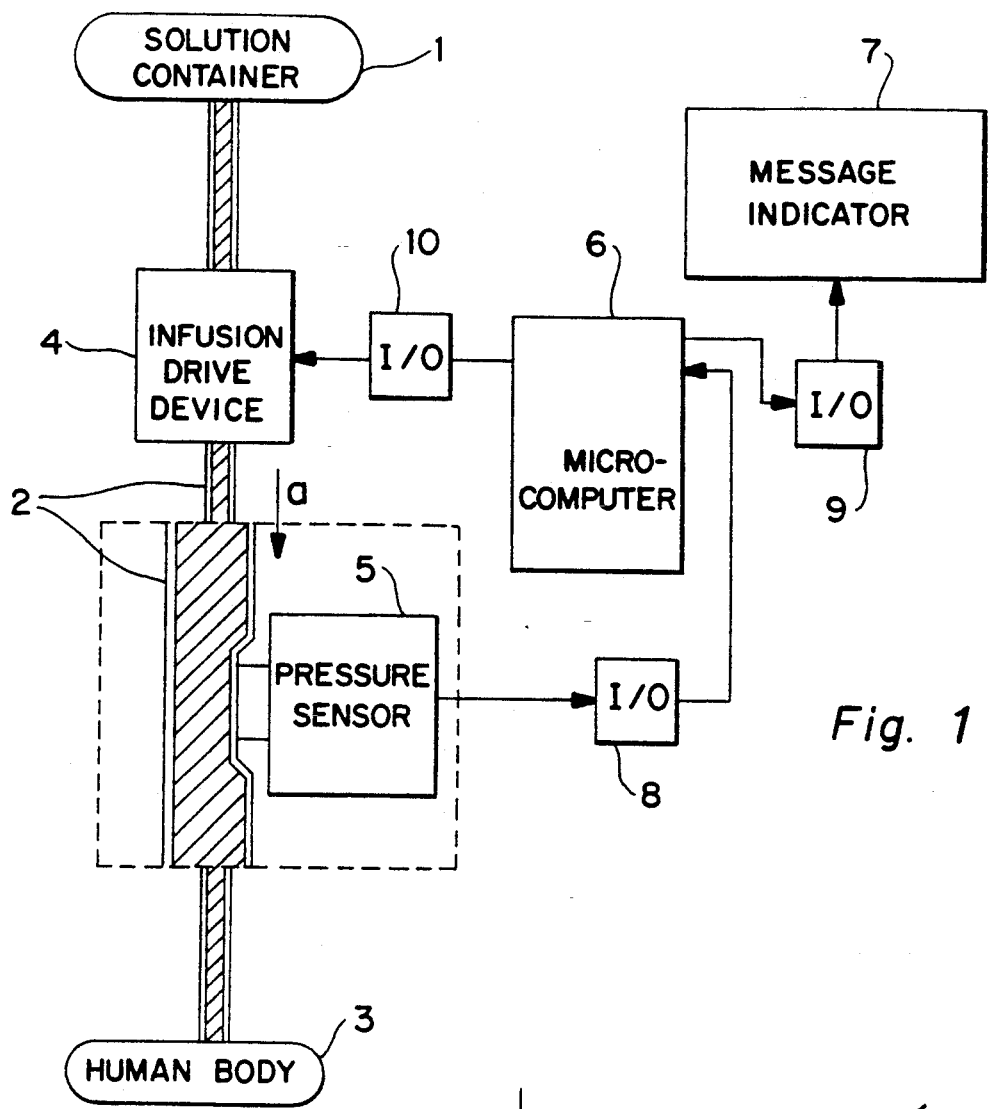
FIG. 1 is a schematic diagram showing the entire infusion device in accordance with the present invention.
FIG. 2 is a graph showing the characteristic of a sensor.

Referring to FIG. 1 showing the entire construction of an infusion device according to an embodiment of the present invention, an infusion drive means 4 operates to infuse a drip infusion contained in an solution container 1 into the human body 3 through a tube 2. A sensor 5 having a function of detecting a tube occlusion is mounted on the tube 2 in contact therewith in the downstream side of the infusion drive means 4. The tube 2 is made of an elastic material so that the outer diameter varies according to the change of the internal pressure thereof. The sensor 5 positioned in contact with the tube 2 detects the change of the outer diameter of the tube 2 to find the change in tube internal pressure. As shown in FIG. 2, the sensor 5 is one whose signal output varies linearly in response to change the outer diameter of the tube 2. In FIG. 2, reference numeral R0 denotes the outer diameter of the tube 2 in a normal condition and R1 denotes the outer diameter thereof detected by the sensor 5 when the diameter thereof has expanded as a result of a tube occlusion which has occurred in the downstream side thereof.

The sensor 5 is selected from a semiconductor sensor, a core-equipped coil sensor, a force displacement transducer, a distortion gauge or the like providing that its resistance value, electric current value, voltage, and oscillation frequency value linearly change.

Figure 3:
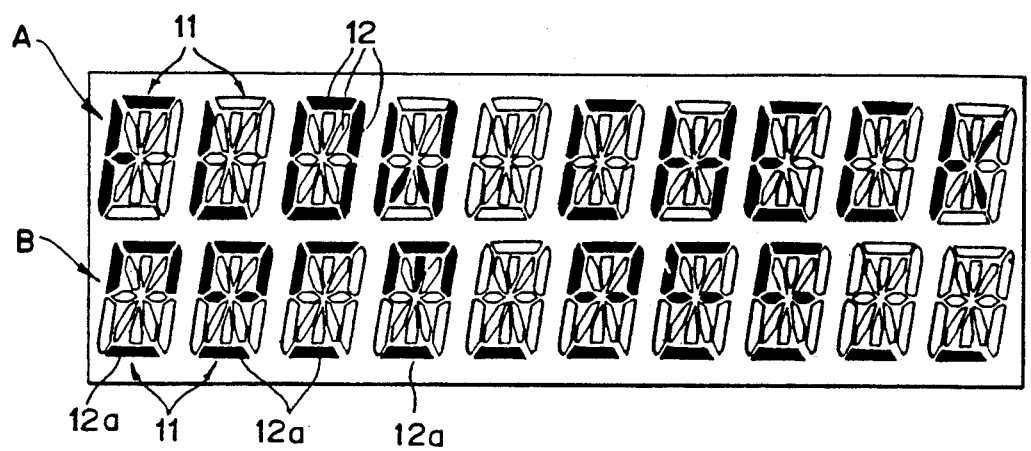
FIGS. 3 and 4 are views showing a message indicator in accordance with the present invention.

The sensor 5 is connected to a microcomputer 6, thus continuously outputting data indicative of the change of the internal pressure of the tube 2 to the microcomputer 6. A message indicator 7 as shown in FIG. 3 is connected with the microcomputer 6, thus in response to an instruction signal outputted from the microcomputer 6, the internal pressure of the tube 2 is displayed as information easy for a nurse or hospital staff to observe. The microcomputer 6 is connected to a motor (not shown) for driving the infusion drive means 4, thus controlling the infusion drive means 4 so as to stop it from operating when the internal pressure of the tube 2 exceeds a predetermined value. Reference numerals 8, 9, and 10 denote interfaces connected between the microcomputer 6 and the sensor 5, between the microcomputer 6 and the message indicator 7, between the microcomputer 6 and the infusion drive means 4, respectively.

As shown in FIG. 3, the message indicator 7 has a plurality of alphanumeric display elements (ten display elements 11 in the embodiment) in two rows, the upper and the lower row, for displaying alarm information. The display elements 11 in the upper row (A) are used to display a warning message in the English language. More specifically, as the black-painted segments 12 of the display elements 11 in the upper row (A) are energized, these segments 12 illuminate in a pattern to display "FLOW CHECK". In the lower row (B), the internal pressure of the tube 2 is displayed in the English language by the upper half segments 12 of the display elements 11 and the horizontal bar segments 12a in the lowermost line are used to display the internal pressure of the tube 2 in the form of a bar graph. Thus, in the example illustrated, in the lower row (B), the upper half segments 12 display the internal pressure of the tube 2 as "NORM OCC" (normal occlusion) which means that the internal pressure of the tube 2 has not reached the occlusion deciding value and the bar segments 12a in the lowermost line are sequentially energized from left to right in proportion to the increase of the internal pressure of the tube 2. In FIG. 3, all the bar segments 12a are energized, which means that the internal pressure of the tube 2 is so high that the tube 2 is immediately before the tube 2 is occluded.

Figure 4:
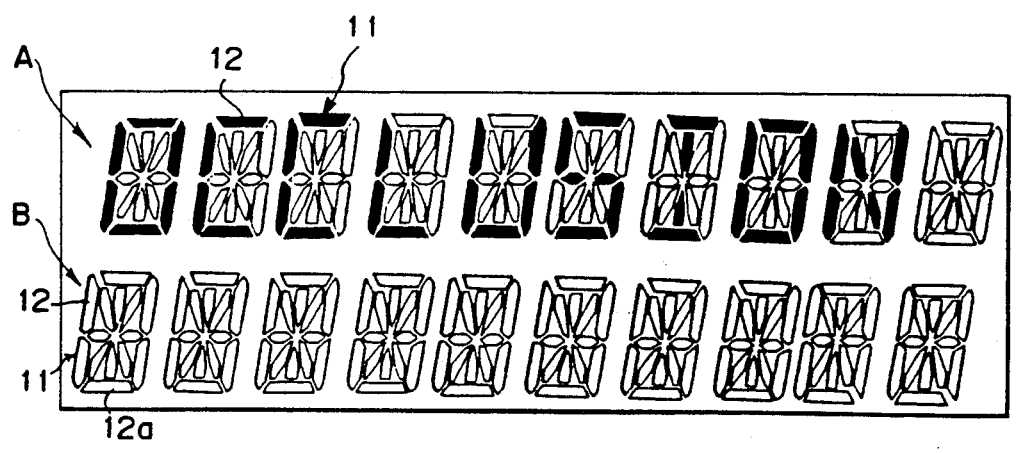

When the infusion drive means 4 is stopped based on the decision that the tube 2 has been occluded, the message indicator 7 displays "OCCLUSION" as shown in FIG. 4.

In the message indicator 7, the internal pressure of the tube 2 is not only displayed by the alphanumeric display elements 11 in English but also displayed as a bar graph by utilizing some segments of the alphanumeric display elements 11. Thus, the user such as a nurse or hospital staff can easily know the quantitative change of the internal pressure of the tube 2 from the bar graph display.

Figure 5:
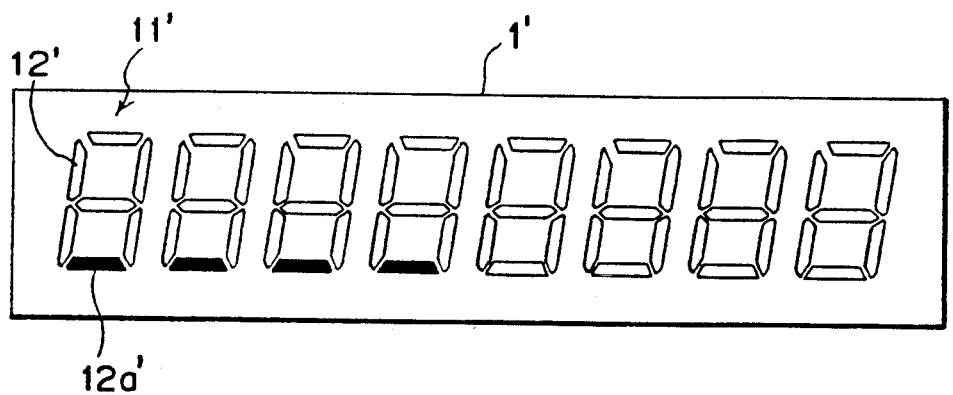
FIG. 5 is a view showing another message indicator in accordance with the present invention.

The method for displaying the internal pressure of the tube 2 is not limited to the above-described embodiment. The following display methods can also be carried out: The upper half of the lower row (B) is used to digitally display the internal pressure of the tube 2 instead of a message in the English language. The upper row (A) is used to display the internal pressure of the tube 2 in English and the lower row (B) is utilized for a bar graph display. In the above-described embodiment, the internal pressure of the tube 2 is displayed in the two rows, however, it may be displayed in only one row. This one row may be so arranged that by switching the mode of display sequentially, a display in English first appears and, then, a digital display appears, followed by a bar graph display. Instead of the alphanumeric display elements 11 of a message indicator 7', numerical display elements 11' each comprising seven segments 12' as shown in FIG. 5, may be used. According to this display method, if two rows are provided, the upper row is used to make a digital display and the lower row is used to make a bar graph display. If only one row is provided, first, the internal pressure of the tube 2 is digitally displayed, then it is displayed by a bar graph display.

Figure 6:
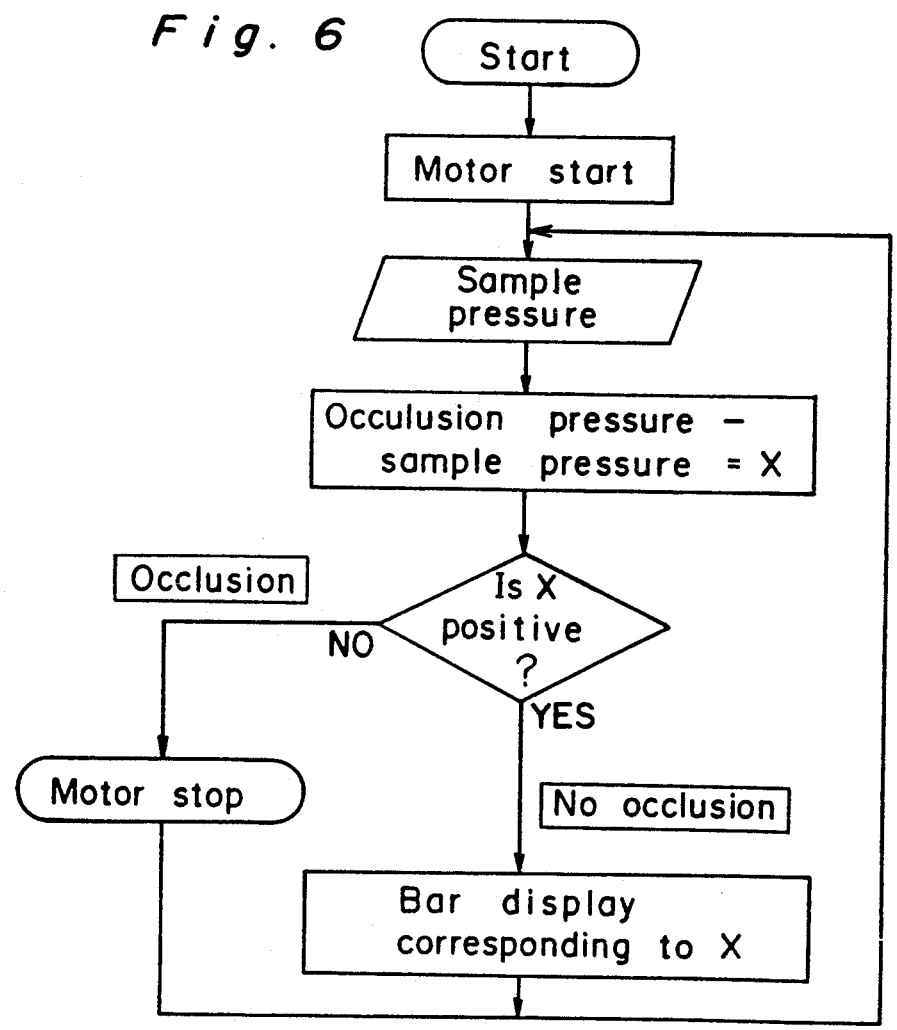
FIG. 6 is a flowchart for describing the operation of the infusion device in accordance with the present invention.

Signals outputted from the sensor 5 are processed by the microcomputer 6 based on the flowchart of FIG. 6. According to the instruction of the microcomputer 6, the segments 12 of the indication elements 11 are energized or deenergized. The operation of device according to the embodiment is described with reference to the flowchart of FIG. 6.

A delivery of an infusion fluid is started by the start of the motor for operating the infusion drive means 4. The fluid is supplied from the solution container 1 to the human body 3 through the tube 2. The pressure of fluid flowing though the tube 2 is sampled by the sensor 5 in a predetermined period of time and data indicative of the sampled value is outputted to the microcomputer 6. If the difference (X) obtained by subtracting the sampled value from a predetermined tube occlusion detecting reference value stored in the memory of the microcomputer 6 is positive, i.e., if the occlusion detection pressure is greater than the sample pressure, it is decided that the tube 2 is not occluded and the internal pressure of the tube 2 is detected according to the difference (X) and displayed by the message indicator 7. That is, if the difference (X) is large, it is decided that the internal pressure of the tube 2 is small, so that only the bar segment 12a positioned on the left side is energized. The remaining bar segments 12a are sequentially energized one by one with the reduction of the difference (X).

Thus, a user such as the nurse observing a patient having infusion into his/her body, is easily capable of monitoring the quantitative change of the internal pressure of the tube 2 according to the increase or decrease of the length of the bars. Accordingly, if the bar is rapidly elongated, i.e., if the internal pressure of the tube 2 rapidly increases, the nurse can see that patient's turning in bed has caused the tube 2 to be occluded. Thus, the nurse can remove the cause and return the increased internal pressure of the tube 2 to a normal pressure.

If the difference X is negative, that is, if the sampled pressure is greater than the predetermined occlusion detecting reference pressure, it is decided that the tube 2 has become occluded. When the tube 2 is occluded, simultaneously with the display of "OCCLUSION"

made on the message indicator 7, the microcomputer 6 generates an instruction to stop the motor for driving the infusion drive means 4.

As described above, in the message indicator for displaying the tube internal pressure, the segments of the alphanumeric or numeric display element are used to display the internal pressure of the tube by the bar graph. Therefore, the length of the bar allows the user, such as a nurse or the hospital staff, to easily find the quantitative change of the internal pressure of the tube. That is, the user can find out whether or not the tube is being occluded. Further, an alarm sounds when the tube is occluding, so that the user can remove the cause of the occlusion and restore the tube-occluded condition to a normal condition before the delivery of the infusion fluid is stopped.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A display device for indicating the internal pressure of a tube of an infusion device having an infusion drive means for supplying an infusion fluid from a solution container to the human body through the tube and a sensor for detecting the internal pressure of the tube, comprising:
    a message indicator for displaying the internal pressure of the tube detected by said sensor;
    said message indicator including at least one row of alphanumeric display elements for selectively generating a text display, a digital display, or a bar graph display, and being indicative of the qualitative change and the quantitative change in the internal pressure of the tube as detected by said sensor;
    said bar graph display further being used to display the quantitative change in the sensor detected pressure;
    wherein said at least one row of display elements of said message indicator comprises an upper row and a lower row of alphanumeric display elements;
    said display elements of the upper row being used to generate a text display of information regarding the operating condition of the tube and the upper half segments of the display elements of the lower row being used to also display text information regarding the internal pressure of the tube while the segments of horizontal bars in the lowermost line of the lower row are used to display a bar graph of the internal pressure of the tube.

2. A device as claimed in claim 1, and additionally including a microcomputer, and wherein said sensor, message indicator, and infusion drive means are connected to said microcomputer,
    said microcomputer comparing data indicative of a pressure inputted thereto from said sensor with a predetermined tube occlusion detecting reference pressure so as to determine whether or not the internal pressure of the tube is greater than said reference pressure and generates an instruction coupled to said message indicator whereby the display elements thereof generate a visual display based on the pressure comparison and additionally generates an operation stop instruction coupled to said infusion drive means when the internal pressure of the tube has reached the tube occlusion detecting reference pressure.

3. A device as claimed in claim 1, wherein said at least one row of alphanumeric display elements of said message indicator sequentially generates said text display, then said digital display and thereafter said bar graph display.

4. A device as claimed in claim 1 wherein said text display is in the English language.

5. A device as claimed in claim 1 wherein said information of said text display includes alarm information.

6. A display device for indicating the internal pressure of a tube of an infusion device having an infusion drive means for supplying an infusion fluid from a solution container to the human body through the tube and a sensor for detecting the internal pressure of the tube, comprising:
    a message indicator for displaying the internal pressure of the tube detected by said sensor;
    said message indicator including at least one row of alphanumeric display elements for selectively generating a text display, a digital display, or a bar graph display, and being indicative of the qualitative change and the quantitative change in the internal pressure of the tube as detected by said sensor;
    said bar graph display further being used to display the quantitative change in the sensor detected pressure, wherein said at least one row of alphanumeric display elements of said message indicator sequentially generates said text display then said digital display and thereafter said bar graph display.

7. A device as claimed in claim 6, and additionally including a microcomputer, and wherein said sensor, message indicator, and infusion drive means are connected to said microcomputer,
    said microcomputer comparing data indicative of a pressure inputted thereto from said sensor with a predetermined tube occlusion detecting reference pressure so as to determine whether or not the internal pressure of the tube is greater than said reference pressure and generates an instruction coupled to said message indicator whereby the display elements thereof generate a visual display based on the pressure comparison and additionally generates an operation stop instruction coupled to said infusion drive means when the internal pressure of the tube has reached the tube occlusion detecting reference pressure.

8. A device as claimed in claim 6 wherein said text display is in the English language.

9. A device as claimed in claim 6 wherein said information of said text display includes alarm information.

* * * * *